United States Patent [19]
Holmes

[11] Patent Number: 6,123,437
[45] Date of Patent: Sep. 26, 2000

[54] EASY ACCESS LIGHT BOX

[75] Inventor: David Paul Holmes, Santa Barbara, Calif.

[73] Assignee: Integra Medical, Camarillo, Calif.

[21] Appl. No.: 09/089,980

[22] Filed: Jun. 3, 1998

[51] Int. Cl.[7] .................................................. F21V 19/02
[52] U.S. Cl. ......................... 362/372; 362/572; 362/804
[58] Field of Search .................................... 362/372, 573, 362/804, 25, 29, 572; 433/25, 29

[56] References Cited

U.S. PATENT DOCUMENTS

| | | | |
|---|---|---|---|
| 4,623,217 | 11/1986 | Hallen . | |
| 5,134,469 | 7/1992 | Uchimurn | 358/98 |
| 5,230,555 | 7/1993 | Stephenson et al. | 362/32 |
| 5,243,500 | 9/1993 | Stephenson et al. | 362/32 |
| 5,283,718 | 2/1994 | Stepjenson et al. | 362/32 |
| 5,295,052 | 3/1994 | Chin et al. | 362/32 |
| 5,309,330 | 5/1994 | Pillers et al. . | |
| 5,672,881 | 9/1997 | Striepeke et al. | 250/461.2 |
| 5,766,006 | 6/1998 | Murljacic | 433/26 |

*Primary Examiner*—Sandra O'Shea
*Assistant Examiner*—John A. Ward
*Attorney, Agent, or Firm*—Blakely, Sokoloff, Taylor & Zafman LLP

[57] ABSTRACT

According to one embodiment, a light box for use with a dental intraoral camera is disclosed. The light box having a lamp inside is coupled to the dental intraoral camera via fiber optic cables. The light box allows easy access to the lamp for lamp replacement by pulling a tray out containing the lamp.

18 Claims, 3 Drawing Sheets

EASY ACCESS LIGHT BOX

BACKGROUND OF THE INVENTION (1) Field of the Invention

The present invention generally relates to devices containing a light source. More specifically, the present invention relates to devices which provide high intensity light for surgical or industrial instruments which incorporate fiber optic cables.

(2) Description of the Related Art

Electronic handheld cameras configured with intraoral imaging optics ("intraoral cameras") are used for capturing images of the inside of a patient's mouth. The camera typically has an elongated body that contains an image sensor and optics. The optics and the sensor are designed for capturing images of the inside of the mouth when the distal or viewing end of the camera is inserted into the patient's mouth. Wires carrying electronic signals typically connect the image sensor to the proximal end of the camera where a communication interface is provided to an image processing system or display monitor that allows manipulation and display of the images. By viewing the displayed images, a diagnosis can be made and appropriate treatment prescribed.

For illuminating the inside of the mouth, a fiber optic cable typically is used to transmit light to the distal or viewing end of the camera. The light is generated by a high intensity light source such as a lamp or bulb typically held in a "light box." The light box is normally intended to supply light to intraoral cameras. However, the light box may also be used to supply light to other devices, such as endoscopes.

FIG. 1 shows a schematic of a prior art intraoral camera as an example of a medical device using such a light box. Intraoral camera 48 is connected to a light box 10 by a fiber optic cable 11. Light box 10 may be placed on a tabletop or mounted up on a wall, stand, or work bench. Light box 10 includes other elements not shown, such as a lamp, a holder, and an optical system comprising a lens assembly for focusing light from the lamp to the fiber optic cable 11.

Light boxes typically operate at high power levels to provide the required intensity of light. Also, because fiber optic cables exhibit losses during transmission of the light, the lamp used in the light box must admit light of a high intensity and is often a high-power lamp. These lamps are typically short-lived and need periodic replacement. Oftentimes, to prevent lamp failures during a surgical procedure, it is desirable to replace the lamp before it actually ceases providing light.

Existing light boxes have several drawbacks. One such drawback is that it is difficult to replace the lamp because the light boxes often have complicated assemblies. For some light boxes, the light box must be partially disassembled to replace the lamp. For the light boxes to function optimally, it is also crucial for the lamp to be correctly placed in the holder to ensure proper alignment of the lamp on the optimum light path. In addition, disassembly by untrained persons may result in an electrical shock to the persons and damage to the light box. For these reasons, -some manufacturers of light boxes require returning the entire light box back to them for lamp replacement. This also results in down time in the use of the light box.

Therefore, it is desirable to provide a light box that allows easy access to the lamp for lamp replacement.

SUMMARY OF THE INVENTION

According to one embodiment, the present invention provides a light box for use with a dental intraoral camera. The light box having a lamp inside is coupled to the dental intraoral camera via fiber optic cables. The light box allows easy access to the lamp for lamp replacement by pulling a tray out containing the lamp.

BRIEF DESCRIPTION OF THE DRAWINGS

The features, aspects, and advantages of the present invention will become more fully apparent from the following detailed description, appended claims, and accompanying drawings in which:

DETAILED DESCRIPTION OF THE INVENTION

The present invention provides a light box that allows easy access for an operator to replace the lamp. The light box comprises a tray and a housing having an opening. The tray holding the lamp slides in and out of the opening of the housing. In one position, when the tray is substantially inside the housing, the tray makes electrical connection with the housing. In another position, when the tray is substantially outside the housing, the tray does not make electrical connection with the housing and an operator may then replace the lamp.

Figure 1:
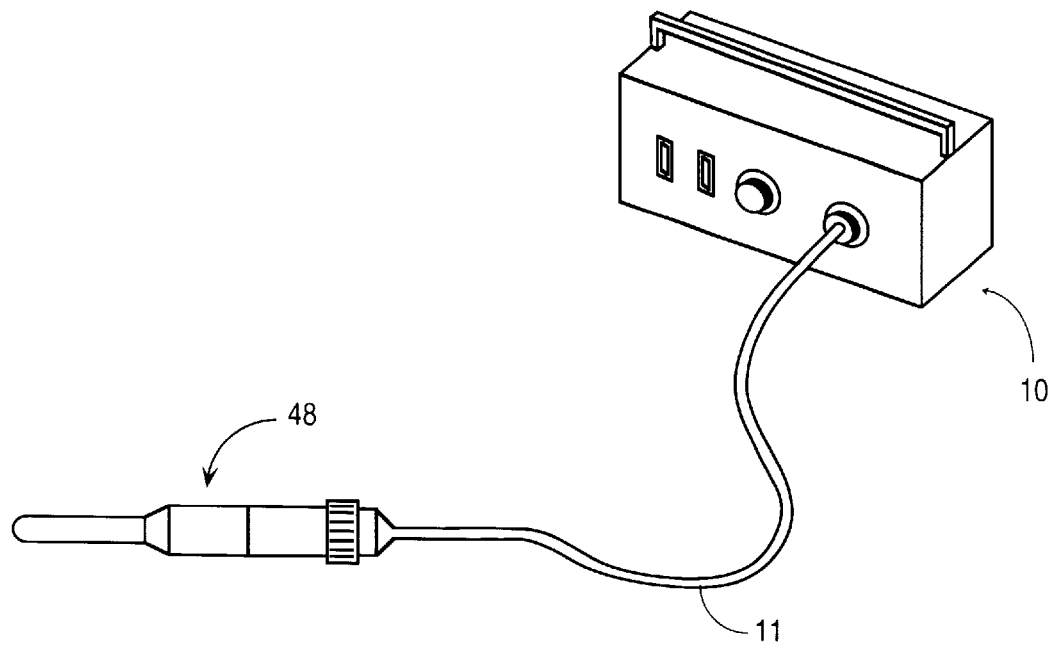
FIG. 1 shows a schematic of a prior art intraoral camera connected to a light box by a fiber optic cable.
Figure 2:
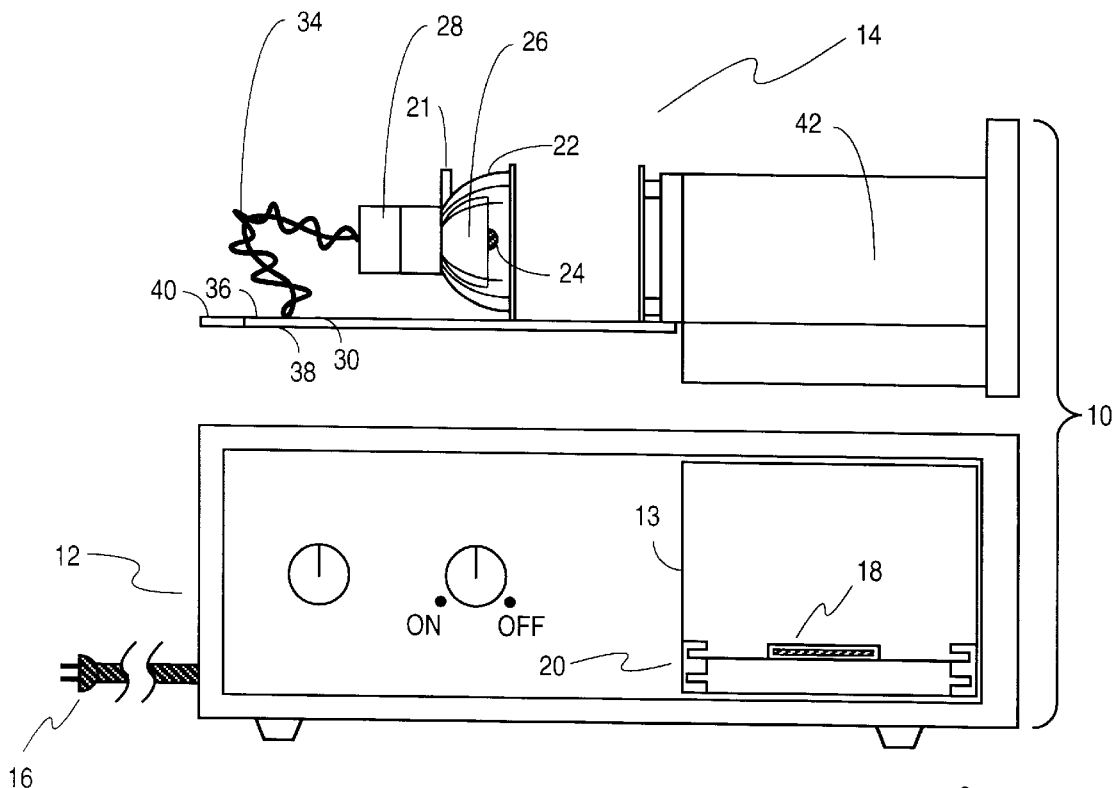
FIG. 2 shows a cross-sectional view of a light box having a housing and a tray according to one embodiment of the present invention.

FIG. 2 shows a cross-sectional view of a light box 10 having a housing 12 and a tray 14 according to one embodiment of the present invention. The light box 10 is normally intended for use by dental personnel for supplying light to dental intraoral cameras. However, it is to be understood that the light box 10 may be used to supply light to other devices, such as endoscopes.

The light box 10 may include brackets or other mounting assemblies (not shown) for convenient mounting on a wall, stand, or work bench. Electrical power is supplied to the housing 12 via a cable 16. The housing 12 houses circuitry for a user interface for controlling the light box 10 and/or a camera processing unit (not shown). The housing 12 includes circuitry for turning a lamp 24 on or off. As those skilled in the art will appreciate, such circuit implementations are well-known and are not described here in detail. In an alternative embodiment, circuitry for adjusting the light intensity for the type of work to be performed may be included. The housing 12 may also include a mating plug 18 mounted in the housing 12 to electrically engage the tray 14 when the tray 14 is correctly installed in the housing 12. The mating plug 18 provides electrical power to the lamp 24. If the tray 14 is removed from the housing 12, or is incorrectly installed, the matching connectors cannot make contact.

In one embodiment of the present invention, the housing 12 has an opening 13 in the front thereof which the tray 14 slides in and out of. It is easier for an operator to gain access to the lamp 24 for the purpose of lamp replacement when the tray 14 slides out the front of the light box 10. This is especially true when the light box 10 is mounted in a way, such as in the inside corner of a desk or underneath a work bench, when access to the lamp 24 by way of the top, sides, or the rear of the light box 10 is restricted.

The housing 12 has guides 20 mounted in the opening 13 in such a way that the tray 14 slidably engages the guides 20 for freely sliding in and out of the front of the housing 12. It is to be appreciated that numerous types of guides may be employed such that the tray 14 may slide freely within the guides 20 without departing from the scope of the present invention. In one embodiment of the present invention, the guides 20 is an extruded aluminum rail guide containing grooves sized and spaced such that the tray 14 may slide freely within them.

The tray 14 comprises a holder 22, the lamp 24, a reflector assembly 26, a socket 28, and a base plate 30. The tray 14 slides out the front of the housing 12 in order to gain access to the lamp 24 for the replacement of such.

The holder 22 is mounted on the base plate 30 and is designed to hold the lamp 24. The holder 22 may be constructed of any such heat resistant material such as ceramic or metal. According to one embodiment of the present invention, the holder 22 is constructed of a metal bracket designed to hold the lamp 24 in such a way as to have repeatable mechanical alignment. The metal bracket includes a lever 21 that is manually used to eject the lamp 24 for the purpose of replacement.

The lamp 24 is used in general light source devices and may include, for example, xenon lamps, halogen lamps, and metal halide lamps. These lamps 24 are ordinarily used in combination with the reflector assembly 26 in such a way as to focus the light onto a spot of a known size at a known distance. For instance, the reflector assembly 26 may include reflecting mirrors for transforming a light bundle emitted from the lamp 24 into a parallel light bundle and collector lenses for imaging or collecting rays reflected from the reflecting mirrors onto the entrance end surface of a fiber optic cable or fiber optic cable bundle. It is to be noted that a light guide other than a fiber bundle may also be used in the present invention.

The socket 28 plugs onto the back of the holder 22 in a removable fashion. The socket 28 receives electrical power from electrical leads 34 to supply electrical power to the lamp 24. According to one embodiment of the present invention, the electrical leads 34 are soldered onto the base plate 30. The socket 28 makes electrical contact between the lamp 24 and the base plate 30 for the purpose of delivering electrical power to the lamp 24 received from the electrical leads 34. Instead of line power, a battery (not shown) may be used as a power supply for the lamp 24. The battery may be any type of battery, e.g., a dry battery or a rechargeable nickel-cadmium battery.

The base plate 30 slidably engages the guides 20 of the housing 12 to freely slide in and out of the front of the housing 12. The base plate 30 may be fabricated of a metal or nonmetal material. It is to be appreciated that numerous materials may be used as the base plate 30 without departing from the scope of the present invention. In one embodiment of the present invention, the base plate 30 comprises a printed wiring board designed in a way such that the holder 22 and the socket 28 is mounted on the base plate 30. The base plate 30 includes a first edge 36 and a second edge 38 which can be received by corresponding the guides 20 mounted in the housing 12 to slide within the guides 20. The base plate 30 includes a connector 40 which engages the mating plug 18 mounted in the housing 12 when the tray 14 is correctly installed in the housing 12. The mating plug 18 provides electrical power to the lamp 24. If the tray 14 is removed from the housing 12, or is incorrectly installed, the mating connectors cannot make contact. The tray 14 may also include a fan (not shown) to channel hot air produced by the lamp 24 outside the light box 10, thereby cooling the lamp 24, the printed wiring board and other elements of the tray 14.

The tray 14 may also include a receptacle 42 for inserting a camera processing unit into. As those skilled in the art will appreciate, it is equally permissible for the camera processing unit to be inserted into the opening of the housing 12 without the need for the receptacle 42. Alternatively, the camera processing unit may be coupled to a module in which the module itself docks into the receptacle 42.

Figure 3:
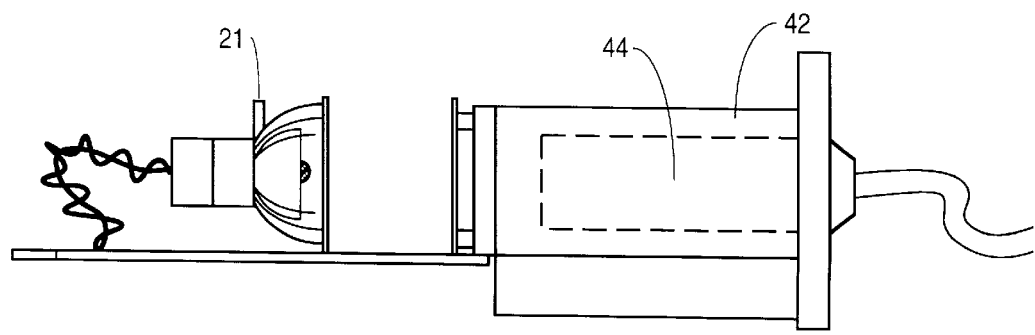
FIG. 3 shows a cross-sectional view of the tray where a camera processing unit is inserted into the receptacle according to one embodiment of the present invention.

FIG. 3 shows a cross-sectional view of the tray 14 where the camera processing unit 44 is inserted into the receptacle 42 according to one embodiment of the present invention. The receptacle 42 allows for optical and electrical connections with the camera processing unit 44. The receptacle 42 is connected to one end of the base plate 30 and is disposed to face the holder 22. The receptacle 42 includes an optical interface (not shown) for coupling to the lamp 24. The optical interface is for making an optical connection with the camera processing unit 44. The receptacle may also contain electrical interface (not shown) for receiving electrical power, the electrical interface for making electrical connection with the camera processing unit 44. The receptacle 42 may include other components such as a fiber optic alignor (not shown) for aligning a fiber optic cable connected to the receptacle 42 for optimal light transmission.

Figure 4:
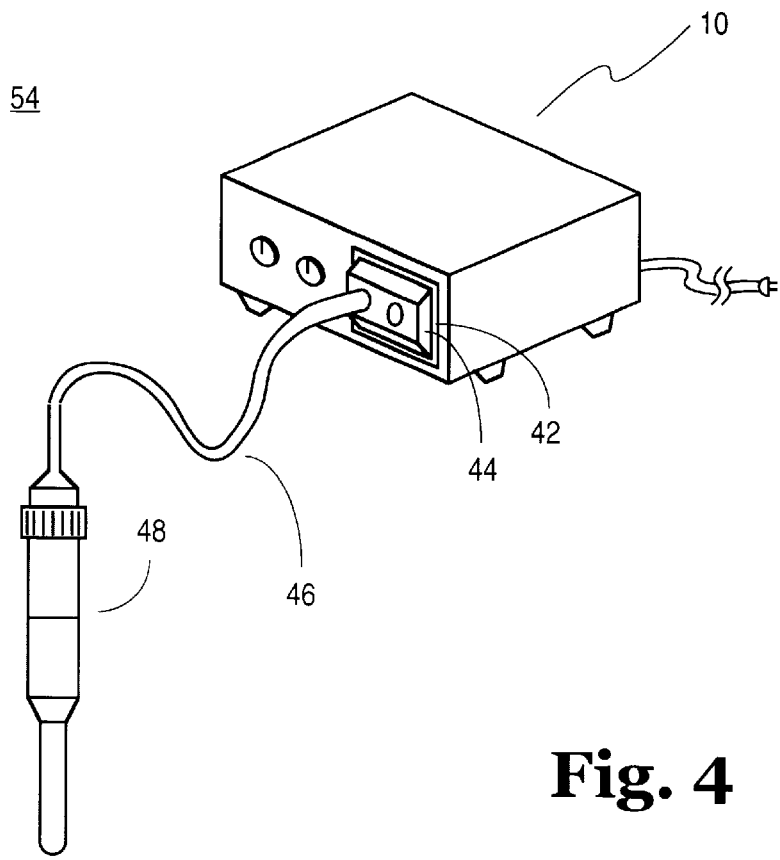
FIG. 4 shows a schematic of an imaging system having a light box, a camera processing unit, a cable, and an intraoral camera according to one embodiment of the present invention; and, FIG. 5 shows a schematic of an imaging system having a light box, a camera processing unit, a cable, an intraoral camera, and a display monitor according to another embodiment of the present invention.

FIG. 4 shows a schematic of an imaging system 54 having a light box 10, a camera processing unit 44, a cable 46, and an intraoral camera 48 according to one embodiment of the present invention. The intraoral camera 48 contains an image sensor (not shown) for capturing an image and converting the light energy to electrical energy. The image sensor may be fabricated with complementary metal oxide semiconductor (CMOS) devices or charge coupled devices (CCD). The electrical energy which may be digital or analog signals from the image sensor may be processed by the camera processing unit 44 and the corresponding image displayed on a display monitor.

The camera processing unit 44 for processing electrical signals may be fabricated as part of the light box 10, as a separate unit, or as part of the intraoral camera 48. It is to be appreciated that numerous kinds of camera processing units 44 could be used without departing from the scope of the present invention. In one embodiment of the present invention, the camera processing unit 44 is fabricated as a separate unit and is designed to be inserted into the receptacle 42.

The intraoral camera 48 is connected to the camera processing unit 44 via the cable 46. The cable 46 may be a fiber optic cable. In one embodiment of the present invention, the cable 46 is a combined electrical cable and a fiber optic cable. The electrical cable carries the electrical signals generated by the image sensor for processing by the camera processing unit 44. The electrical cable is connected to an electrical connector (not shown) in the camera processing unit 44. The fiber optic cable carries the light generated from a lamp and is connected to an optical connector (not shown) in the camera processing unit 44. The optical connector couples to the optical interface (not shown) of the receptacle 42, and the electrical connector (not shown) couples to the electrical interface (not shown) of the receptacle 42. It is to be understood that a variety of other optical and electrical connections between the intraoral camera 48 and the light box 10 may be possible without departing from the scope of the present invention.

Figure 5:
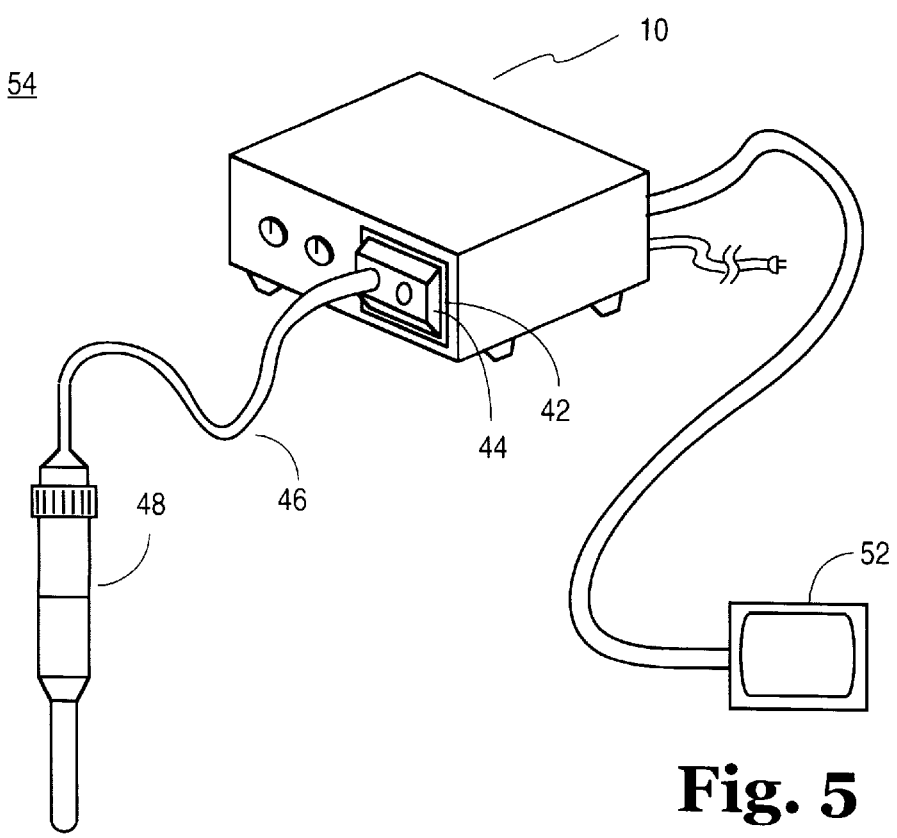

FIG. 5 shows a schematic of an imaging system having a light box 10, a camera processing unit 44, a cable 46, an intraoral camera 48, and a display monitor 52 according to another embodiment of the present invention. The intraoral camera 48 is connected to the light box 10 via the cable 46. The display monitor 52 is connected to the back of the light box 10. The display monitor 52 generates a picture for an operator to view the inside or outside of a patient's mouth.

In the foregoing specification, the invention has been described with reference to specific embodiments thereof. It will however be evident that various modifications and changes can be made thereto without departing from the broader spirit and scope of the invention as set forth in the appended claims. The specification and drawings are, accordingly, to be regarded in an illustrative rather than a restrictive sense. Therefore, the scope of the invention should be limited only by the appended claims.

What is claimed is:

1. A lighting device comprising:
   a housing having an opening; and,
   a tray for holding a lamp, said tray movably mounted in said opening between a first position and a second position, wherein in said first position, said tray is substantially inside said housing, and in said second position, said tray is substantially outside said housing, and in said second position, said tray is substantially outside said housing for accessing said lamp, the tray having a receptacle inserted into the housing through the opening, the receptacle having a frontal opening to receive a camera processing unit therethrough, the receptacle having an optical interface to optically couple the lamp and the camera processing unit, and an electrical interface to power the camera processing unit.

2. The lighting device of claim 1 wherein said opening has rails configured to movably engage said tray.

3. The lighting device of claim 2 wherein said tray slides horizontally in said opening.

4. The lighting device of claim 2 wherein said tray comprises:
   a base plate having two edges configured to slidably engage said rails, the receptacle being coupled to the base plate; and a holder mounted on said base plate, said holder configured to hold said lamp, and wherein the lighting device further includes
   a socket configured to supply electrical power to said lamp.

5. The lighting device of claim 4 wherein said base plate comprises a printed wiring board.

6. The lighting device of claim 5 wherein said base plate comprises a connector for providing electrical power to said lamp.

7. The lighting device of claim 1 further comprising a lever being manually operable for ejecting said lamp.

8. The lighting device of claim 1 further comprising an optical connector in said camera processing unit configured to couple said optical interface.

9. The lighting device of claim 1 further comprising an electrical connector in said camera configured to couple said electrical interface.

10. The lighting device of claim 1 further comprising circuitry configured to supply electrical power to said lamp.

11. The lighting device of claim 1 further comprising circuitry for a user interface to control said lighting device.

12. An imaging system comprising:
   a lighting device having:
   a housing having an opening;
   a tray holding a lamp, said tray movably mounted in said opening between a first position and a second position, wherein in said first position, said tray is substantially inside said housing, and in said second position, said tray is substantially outside said housing for accessing said lamp;
   a camera processing unit coupled to said tray to be inserted into said housing through the opening;
   the tray having a receptacle to be inserted into the housing through the opening, the receptacle having a frontal opening to receive the camera processing unit therethrough, the receptacle having an optical interface to optically couple the lamp and the camera processing unit and an electrical interface to power the camera processing unit; and
   a light transmission medium coupled to said camera processing unit for guiding light from the lamp to an intraoral camera.

13. The imaging system of claim 12 wherein said opening has rails configured to movably engage said tray.

14. The imaging system of claim 13 wherein said tray further comprises:
   a base plate having two edges configured to slidably engage said rails;
   a holder mounted on said base plate, said holder configured to hold said lamp; and, wherein the
   receptacle is coupled to said base plate.

15. The imaging system of claim 14 further comprising an optical connector in said camera processing unit configured to couple said optical interface.

16. The imaging system of claim 15 further comprising an electrical connector in said camera processing unit configured to couple said electrical interface.

17. The imaging system of claim 12 further comprising:
   a display monitor coupled to said housing.

18. The imaging system of claim 12 wherein said light transmission medium comprises fiber optic cables.

* * * * *